United States Patent
Mantovani et al.

(10) Patent No.: US 9,081,018 B2
(45) Date of Patent: Jul. 14, 2015

(54) DIAGNOSTIC TEST FOR INFLAMMATORY ENDOTHELIAL DYSFUNCTIONS IN PREGNANCIES

(75) Inventors: Alberto Mantovani, Milan (IT); Cecilia Garlanda, Milan (IT); Andrea Doni, Milan (IT); Irene Cetin, Milan (IT)

(73) Assignee: Humanitas Mirasole S.p.A., Rozzano (IT)

( * ) Notice: Subject to any disclaimer, the term of this patent is extended or adjusted under 35 U.S.C. 154(b) by 695 days.

(21) Appl. No.: 12/159,724

(22) PCT Filed: Dec. 18, 2006

(86) PCT No.: PCT/EP2006/012168
§ 371 (c)(1),
(2), (4) Date: Aug. 8, 2008

(87) PCT Pub. No.: WO2007/073899
PCT Pub. Date: Jul. 5, 2007

(65) Prior Publication Data
US 2008/0311603 A1 Dec. 18, 2008

(30) Foreign Application Priority Data

Dec. 29, 2005 (EP) .................................... 05028630

(51) Int. Cl.
*C07K 16/24* (2006.01)
*G01N 33/543* (2006.01)
*G01N 33/68* (2006.01)

(52) U.S. Cl.
CPC .............. *G01N 33/689* (2013.01); *C07K 16/24* (2013.01); *G01N 33/543* (2013.01); *G01N 2333/4715* (2013.01); *G01N 2800/368* (2013.01); *G01N 2800/50* (2013.01); *G01N 2800/7095* (2013.01)

(58) Field of Classification Search
CPC ...... C07K 16/18; C07K 16/24; G01N 33/535; G01N 33/543; G01N 33/545; G01N 33/577; G01N 33/689; G01N 2033/50; G01N 2033/53; G01N 2333/435; G01N 2333/4715; G01N 2333/4737; G01N 2800/368; G01N 2800/50; G01N 2800/7095
USPC .................. 435/7.1, 7.24, 7.5, 7.92, 7.94, 28, 435/70.21, 336, 337, 343; 436/510, 518, 436/531, 548, 65, 164; 530/388.24, 388.25, 530/388.7, 389.3, 389.6, 391.1
See application file for complete search history.

(56) References Cited

U.S. PATENT DOCUMENTS

2004/0137544 A1* 7/2004 Latini et al. .................. 435/7.92

FOREIGN PATENT DOCUMENTS

WO WO 2005/106494 11/2005

OTHER PUBLICATIONS

Harlow et al., 1988. Antibodies. A Laboratory Manual, Cold Spring Harbor Laboratory, Cold Spring Harbor. p. 593.*
Muller et al., 2001. Circulating levels of the long pentraxin PTX3 correlate with severity of infection in critically ill patients. Critical Care Med. 29: 1404-1407.*
Kuperminc et al., 1994. Tumor necrosis factor-alpha is elevated in plasma and amniotic fluid of patients with severe preeclampsia. American J. Obstetrics Gynecol. 170: 1752-1759.*
Rinehart et al., 1999. Expression of the placental cytokines tumor necrosis factor alpha, interleukin 1beta, and interleukin 10 is increased in preeclampsia. American J. Obstetrics Gynecol. 181: 915-920.*
Breviario et al., 1992. Interleukin-1-inducible genes in endothelial cells. Journal Biol. Chem. 267: 22190-22197.*
Peri et al., 2000. PTX3, a prototypical long pentraxin, is an early indicator of acute myocardial infarction in humans. Circulation 102: 636-641.*
Redman et al., 2005. Latest advances in understanding preeclampsia. Science 308: 1592-1594.*
Vouret-Craviari et al., 1997. Expression of a long pentraxin, PTX3, by monocytes exposed to the mycobacterial cell wall component lipoarabinomannan. Infection and Immunity 65: 1345-1350.*
Cetin et al., 2009. First trimester PTX3 levels in women who subsequently develop preeclampsia and fetal growth restriction. Acta Obstet. Gynecol. 88: 846-849.*
Hamai et al., 1997. Evidence for an elevation in serum Interleukin-2 and Tumor Necrosis Factor-alpha levels before the clinical manifestations of preeclampsia. American Journal of Reproductive Immunology 38: 89-93.*
Irene Cetin, MD., et al. "Elevated Maternal Levels of the Long Pentraxin 3 (PTX3) in Preeclampsia and Intrauterine Growth Restriction", American Journal of Obstetrics and Gyncology (2006), 194, 1347-53.

* cited by examiner

*Primary Examiner* — Gail R Gabel
*Assistant Examiner* — James L Grun
(74) *Attorney, Agent, or Firm* — Dickstein Shapiro LLP

(57) ABSTRACT

The present invention relates to a diagnostic test for inflammatory endothelial dysfunctions in pregnant women. Particularly, the present invention relates to a method of diagnosing or evaluating the risk of contracting an inflammatory endothelial dysfunction of the maternal compartment comprising the following steps: a) detecting the plasma levels of long pentraxin PTX3 in blood samples taken from a pregnant woman; b) comparing the PTX3 plasma level data, obtained according to step a), with statistically significant PTX3 plasma level data of normal pregnant population.

5 Claims, No Drawings

DIAGNOSTIC TEST FOR INFLAMMATORY ENDOTHELIAL DYSFUNCTIONS IN PREGNANCIES

The present invention relates to a diagnostic test for inflammatory endothelial dysfunctions in pregnant women.

Preeclampsia represents an important cause of maternal as well as perinatal morbidity and mortality. In spite of its relevant epidemiologic impact the complete pathogenesis of this disease still remains unclear, underlining a multi-factorial etiology. The typical clinical manifestations of preeclampsia, including hypertension, proteinuria and the varying degrees of ischemic peripheral organ damage, which typically arise in third trimester of gestation, might be late phenomena of the complex process of embryo implantation. Deficient remodelling of the spiral arteries during the interaction between maternal and fetal sides at the time of trophoblast invasion has been postulated as a cause of placental insufficiency. This would lead to the dismission of inflammatory factors in the systemic maternal circulation. Endothelial dysfunction has been hypothesized to be part of an excessive maternal inflammatory response to pregnancy. Complement activation, activated circulating leukocytes, increased release of reactive oxygen species, as well as increased levels of various inflammatory cytokines in preeclampsia all agree with this hypothesis.

Eclampsia manifests late in a few pre-eclamptic cases and is characterised by the same symptoms of pre-eclampsia with in addition convulsions. Eclampsia is a life-threatening maternal condition.

So far, there are no diagnostic tests that can provide for an early diagnosis of these pathologies.

It is thus a long felt need to provide a method of diagnosing or assessing the risk of contracting pre-eclampsia and/or eclampsia.

Long pentraxin PTX3 (herein below simply indicated as "PTX3") is a recently described inflammatory molecule which belongs to the same family of the well known C-Reactive Protein (CRP). PTX3 differs from CRP in terms of cellular origin, molecular inducers and kinetic of production. It is expressed by different inflammatory cells like endothelial cells, monocytes, macrophages and fibroblasts exposed to inflammatory stimuli. Normally, PTX3 plasma levels increase dramatically during endotoxic shock, sepsis or other inflammatory conditions.

PTX3 is produced at high levels by vessel wall elements, binds to the angiogenic growth factor FGF2 and tunes its action in vitro and in vivo. PTX3 plasma levels are increased in vascular disorders including myocardial infarction and small vessel vasculitis.

We have now surprisingly found that plasma levels of PTX3 in pregnant women correlate with the risk of such women of contracting preeclampsia and eventually eclampsia.

Thus it is a general object of the present invention to provide a diagnostic method for detecting or evaluating the risk of contracting an inflammatory endothelial dysfunction of the maternal compartment, the said method includes evaluating the plasma levels of long pentraxin PTX3 in blood samples taken from pregnant women.

More specifically, it is an object of the present invention to provide a method of diagnosing or evaluating the risk of contracting pre-eclampsia and eclampsia in pregnant women, the said method includes evaluating the plasma levels of long pentraxin PTX3 in blood samples taken from pregnant women.

It is a further object of the present invention to provide a method for an early diagnosis of or evaluating the risk of contracting pre-eclampsia and eclampsia in pregnant women, the said method includes evaluating the plasma levels of long pentraxin PTX3 in blood samples taken from pregnant women in the I and/or II trimester of gestation.

According to a still further object of the present invention, the plasma levels of PTX3 are correlated with the severity of the illness, so that the method of the invention provides a way for diagnosing or evaluating the risk of contracting a mild form or a severe form of the endothelial dysfunction.

It is a further object of the present invention a method for diagnosing or evaluating the risk of contracting IUGR (IntraUterine Growth Restriction) in pregnant women, the said method includes evaluating the plasma levels of long pentraxin PTX3 in blood samples of said pregnant women.

EXPERIMENTAL PART

Patients were recruited among pregnant women according to the following criteria: 44 normal pregnancies; 33 pregnancies complicated by preeclampsia, which was diagnosed in advance; 24 pregnancies complicated by IUGR. Gestational age was determined according to the onset of the last menstrual period and by an ultrasonographic examination performed before 20 weeks of gestation.

Women with physiological pregnancies and normal intrauterine fetal growth were enrolled as normal pregnancies. Exclusion criteria of this group were previous or current maternal diseases, pharmacologic treatment which could influence pregnancy outcome and fetal growth. Fetal growth was documented by ultrasound in utero and confirmed by fetal weight at birth between the 10th and the 90th percentile according to Italian standards for birthweight and gestational age. All normal pregnancies delivered at term, between the 37th and 42nd week.

Maternal blood samples were collected in the I, II and III trimester of gestation at the time of their routine obstetric visit at the hospital. Blood samples of patients with pregnancies complicated by preeclampsia or IUGR were also collected at the time of diagnosis of the gestational disease. Maternal blood was drawn from a brachial vein under fasting conditions and centrifuged. Plasma was then stored at −80° C. until analysis.

Evaluation of Plasma Levels of PTX3 in Blood Samples

The sandwich ELISA for PTX3 was performed. ELISA plates (96 well; Nunc Immuno Plate, MaxiSorp, Nunc) were coated with 100 ng/well of rat monoclonal anti-PTX3 antibody (mAb) MNB4 diluted in coating buffer (15 mM carbonate, $Na_2CO_3+NaHCO_3$, buffer pH 9.6) and were incubated overnight at 4° C. The plates were washed with washing buffer (Dulbecco's phosphate buffered containing 0.05% Tween20) and 300 μl of 5% dry milk were added to block non-specific binding sites. 50 μl of recombinant human PTX3 standards (100 pg/ml to 2 ng/ml) and unknown samples were added in duplicate and incubated for 2 hr at 37° C. After three washes with the washing buffer, 25 ng/well of biotin conjugated PTX3 affinity-purified rabbit IgG were added for 1 hr at 37° C. Wells were extensively washed and incubated with 100 μl of Streptavidin-peroxidase conjugated to dextran backbone (AmDex, Copenhagen, Denmark) diluted 1:4000 for 1 hr at room temperature. After incubation the plates were washed four times and 100 μl of TMB chromogen (BD, Pharmingen) were added. Absorbance values were read at 405 nm in an automatic ELISA reader.

Immunohistochemistry

Pattern and site of expression of PTX3 were studied by immunohistochemistry on placental samples of normal and preeclamptic pregnancies collected at the time of caesarean section. The pathologist was blinded with regard to the groups from which the samples were derived.

Placental samples were fixed in neutral buffered formalin and embedded in paraffin; haematoxylin-eosin stained sections were examined for histological evaluation. For immunhystochemistry analysis 3 μm paraffin embedded sections were cut and mounted on Super-frost slides (Bio-Optica, Milan, Italy); after dewaxing in xylene and rehydrating in ethanol, the sections were pretreated in a microwave oven (2 cycles for 5 minutes each at 780 W, in 0.01 M citrate buffer) and incubated for 2 hr with a polyclonal antibody against human PTX3. The reactions were revealed by non-biotin peroxidase detection system with 3,3'-diaminobenzidine free base as chromogen. Negative controls were obtained by omission of the primary antibody.

Results

Data are presented as mean±SD. Data between normal pregnancies and pregnancies complicated by preeclampsia or IUGR were compared by unpaired Student's test.

Differences were considered statistically significant at $p<0.05$.

Normal and preeclamptic pregnancies have been monitored in the I, II and III trimester. Average gestational age at sampling was 10.1±1.5, 20.6±3.0 and 32.6±3.1 weeks, respectively. Maternal age and basal body mass index (BMI) were similar for the women of the three trimesters.

Nine of the 26 normal III trimester pregnancies were delivered by cesarean section because of breech presentation or previous caesarean section. Preeclamptic pregnancies were delivered significantly earlier than normal pregnancies (32.1±3.6 versus 39.2±1.0 weeks of gestation, $p<0.001$) and always by caesarean section because of fetal compromise or maternal indications. Fetal and placental weights were significantly lower in preeclampsia group compared to normal pregnancies.

In normal pregnancies, PTX3 levels do not change significantly among I (3.09±1.92 ng/ml), II (1.88±0.45 ng/ml) and III (3.01±2.49 ng/ml) trimester.

Preeclamptic patients show significantly higher levels of PTX3 than normal pregnancies of the same sampling gestational weeks (23.3±27.2 ng/ml in preeclamptic patients versus 3.01±2.49 ng/ml in the III trimester; $p<0.001$). The patient having the highest PTX3 level (106.55 ng/ml) also developed eclampsia.

Immunohistochemistry conducted on placental tissues revealed no differences of PTX3 distribution in normal and preeclamptic placentas. In both control and study cases immunostaining for PTX3 was localised in the stromal tissue of the stem villi and in the anchoring villi in a predominant way. Lower immunostaining was found in the matrix of some terminal villi.

The clinical study has also evidenced that the plasma levels of PTX3 are in relationship with the severity of preeclampsia. It has been found that the PTX3 levels in patients affected by a mild form of preeclampsia are 17.7±22.5 ng/ml ($p<0.001$), while in patients with severe preeclampsia the PTX3 plasma levels raised to 24.1±32.2 ng/ml ($p<0.001$).

In another clinical study, the levels of PTX3 were assessed in pregnant women affected by IUGR (IntraUterine Growth Restriction). The same experimental standards of the previous study were used. The PTX3 levels in such IUGR patients were determined as 7.7±12.4 ng/ml ($p<0.05$).

The above results are in line with the suggestion that preeclampsia represents a clinical manifestation of an endothelial dysfunction as part of an excessive maternal inflammatory response to pregnancy. Without to be bound to any theory, the clinical manifestation of preeclampsia in the III trimester of gestation might be late phenomena of the complex process of embryo implantation. This endothelial dysfunction would lead to the activation and dismission of inflammatory factors, like cytokines and growth factors (TNF-alpha, IL-1), in the systemic maternal circulation.

The present invention therefore provides a method of diagnosing or evaluating the risk of contracting an inflammatory endothelial dysfunction of the maternal compartment comprising a first step of detecting the plasma levels of long pentraxin PTX3 in blood samples taken from a pregnant woman.

Particularly, the said inflammatory endothelial dysfunction of the maternal compartment is pre-eclampsia and/or eclampsia.

In another embodiment, the said inflammatory endothelial dysfunction is IUGR (IntraUterine Growth Restriction).

Body samples can be taken during the whole gestation period. However, in order to provide an early diagnosis of or for evaluating the risk of contracting said diseases, the body samples on which the diagnostic method of the invention can be advantageously performed are those taken during the I and/or II trimester of gestation.

Plasma levels of PTX3 can be detected according to the ELISA test described above. However, any other known laboratory test can be used to this end.

The said ELISA test comprises:

i) coating ELISA plates with rat monoclonal anti-PTX3 antibody (mAb) MNB4 (preferably, in amount of 100 ng/well) diluted in a coating buffer (preferably, buffer at pH 9.6);

ii) incubating the said plates at refrigerated temperature (preferably, about 4° C.);

iii) washing the said plates with a washing buffer (preferably, Dulbecco's phosphate buffered containing 0.05% Tween20); iv) adding an amount of 5% dry milk solution apt to block non-specific binding sites;

v) adding the said body sample and incubating for 1-3 hr at 35-40° C.;

vi) adding biotin conjugated PTX3 affinity-purified rabbit IgG and incubating in the conditions of step v);

vii) adding Streptavidin-peroxidase conjugated to dextran backbone diluted 1:4000 and incubating;

viii) adding TMB chromogen and reading absorbance values at 405 nm in an automatic ELISA reader.

The method of the invention further comprises a second step of comparing the PTX3 plasma level data, obtained according to the said first step of detecting, with statistically significant PTX3 plasma level data of normal pregnant population. Generally, for a normal pregnant population a plasma level of about 3 ng/ml has been found to be statistically significant.

Plasma levels of PTX3 that are indicative for a diagnosis of or for evaluating the risk of contracting pre-eclampsia, eclampsia or IUGR are generally above about 3 ng/ml.

Preferably, PTX3 plasma levels above about 10 ng/ml are taken into consideration as an index of or a risk marker for pre-eclampsia and/or eclampsia, while PTX3 plasma levels above about 6 ng/ml are taken into consideration as an index of or a risk marker for IUGR.

More specifically, PTX3 plasma levels up to 40 ng/ml are indicative of a risk marker or a diagnosis of mild preeclampsia, PTX3 plasma levels up to 60 ng/ml are indicative of a risk marker or a diagnosis of severe preeclampsia and PTX3 plasma levels above 70 ng/ml, preferably above 80 ng/ml, are indicative of a risk marker or a diagnosis for eclampsia.

The present invention also relates to a kit for the evaluation of the plasma levels of long pentraxin PTX3 in body samples.

A kit according to the invention may contain ELISA plates coated with rat monoclonal anti-PTX3 antibody (mAb) MNB4. The kit of the invention may further contain recombinant human PTX3 standards (100 pg/ml to 2 ng/ml) and biotin conjugated PTX3 affinity-purified rabbit IgG. Additionally, a washing Dulbecco's phosphate buffer containing 0.05% Tween20 may also be included. Streptavidin-peroxidase conjugated to dextran backbone and TMB chromogen can finally be comprised in the kit of the invention.

The invention claimed is:

1. Method of diagnosing or evaluating a risk of contracting an inflammatory endothelial dysfunction of a maternal compartment, said dysfunction being preeclampsia and/or eclampsia, the method comprising the steps of:

obtaining a blood plasma sample from a pregnant woman in a third trimester of pregnancy;

contacting the blood plasma sample with rat monoclonal anti-PTX3 antibody (mAb) MNB4, and then detecting an amount of long pentraxin PTX3 bound to the anti-PTX3 MNB4 monoclonal antibody to indicate a level of long pentraxin PTX3 in the blood plasma sample; and determining whether plasma level of long pentraxin PTX3 in the blood plasma sample taken from the pregnant woman in the third trimester of pregnancy is above about 3 ng/ml, wherein a level of long pentraxin PTX3 above 3 ng/ml in the blood plasma sample from the pregnant woman indicates that the woman has an increased risk of preeclampsia or eclampsia.

2. The method according to claim 1, wherein PTX3 plasma levels above about 10 ng/ml are considered as an index of or a risk marker for pre-eclampsia and/or eclampsia.

3. The method according to claim 1, wherein PTX3 plasma levels above 70 ng/ml are indicative of diagnosis of or a risk marker for eclampsia.

4. The method according to claim 1, wherein PTX3 plasma levels above 80 ng/ml are indicative of diagnosis of or a risk marker for eclampsia.

5. The method according to claim 1, wherein said steps of contacting and detecting comprise:

i) coating wells of an enzyme-linked immunosorbent assay (ELISA) plate with said rat monoclonal anti-PTX3 antibody MNB4 diluted in a coating buffer;

ii) incubating said plate at refrigerated temperature;

iii) washing said plate with a washing buffer;

iv) adding an amount of 5% dry milk solution apt to block non-specific binding sites in the wells;

v) adding said blood plasma sample to coated wells of the plate to contact the sample with the anti-PTX3 MNB4 monoclonal antibody and incubating for 1-3 hr at 35-40° C. to bind long pentraxin PTX3 in the sample to the coated MNB4 antibody;

vi) washing said plate with a washing buffer;

vii) adding biotin-conjugated PTX3 affinity-purified rabbit anti-PTX3 IgG and incubating in the conditions of step v) to bind the rabbit anti-PTX3 IgG to long pentraxin PTX3 bound to the coated MNB4 antibody;

viii) adding Streptavidin-peroxidase conjugated to dextran backbone diluted 1:4000 and incubating;

ix) adding tetramethyl benzidine (TMB) chromogen and reading absorbance values at 405 nm in an automatic ELISA reader to indicate the amount of bound PTX3; and x) comparing the absorbance values with absorbance values for long pentraxin PTX3 standards to determine the level of long pentraxin PTX3 in the sample.

* * * * *